US008249381B2

(12) United States Patent
Kolterman et al.

(10) Patent No.: US 8,249,381 B2
(45) Date of Patent: Aug. 21, 2012

(54) IMAGE BASED CORRECTION FOR UNWANTED LIGHT SIGNALS IN A SPECIFIC REGION OF INTEREST

(75) Inventors: James C. Kolterman, Libertyville, IL (US); Eric B. Shain, Glencoe, IL (US); Robert C. Gray, Gurnee, IL (US); Shihai Huang, Evanston, IL (US); Gavin Cloherty, Wauconda, IL (US)

(73) Assignee: Abbott Laboratories, Des Plaines, IL (US)

( * ) Notice: Subject to any disclaimer, the term of this patent is extended or adjusted under 35 U.S.C. 154(b) by 0 days.

(21) Appl. No.: 12/707,011

(22) Filed: Feb. 17, 2010

(65) Prior Publication Data

US 2010/0142848 A1    Jun. 10, 2010

Related U.S. Application Data

(63) Continuation of application No. 11/283,365, filed on Nov. 18, 2005, now abandoned.

(51) Int. Cl.
*G06K 9/00* (2006.01)
*G06K 9/40* (2006.01)
(52) U.S. Cl. .................. 382/274; 382/275; 382/129
(58) Field of Classification Search .............. 382/274, 382/129
See application file for complete search history.

(56) References Cited

U.S. PATENT DOCUMENTS

| 3,979,589 A | 9/1976 | Sternberg et al. |
| 5,096,807 A | 3/1992 | Leaback |
| 5,107,422 A | 4/1992 | Kamentsky et al. |
| 5,139,744 A | 8/1992 | Kowalski |
| 6,097,025 A * | 8/2000 | Modlin et al. ........... 250/227.22 |
| 6,238,875 B1 * | 5/2001 | Altieri ......................... 435/7.23 |

(Continued)

FOREIGN PATENT DOCUMENTS

EP     1227311     7/2002

OTHER PUBLICATIONS

Derwent 2003-767566 abstract, Cumme G; Horn A ; Horn L R B ; Rhode H ; Schulze M, Priority-Data: 2002DE-1012557 (Mar. 14, 2002).*

(Continued)

*Primary Examiner* — Michelle Entezari
(74) *Attorney, Agent, or Firm* — McDermott Will & Emery LLP

(57) ABSTRACT

A method for correcting the signal in an image having a plurality of regions of interest, the method comprising the steps of:
(a) providing an image having a plurality of regions of interest, these regions of interest having areas between them;
(b) determining a region of correction between at least two regions of interest;
(c) calculating a correction signal from the region of correction; and
(d) using the correction signal to correct a measured signal from one or more regions of interest.
This invention also provides a method for defining a region of correction for use in a method for correcting the signal in an image having a plurality of regions of interest, the defining method comprising the steps of:
(a) providing an image having a plurality of regions of interest;
(b) extracting geometric information for a plurality of regions of interest;
(c) selecting a location between at least two regions of interest;
(d) selecting at least one parameter to describe regions of correction; and
(e) constructing regions of correction between the at least two regions of interest.

24 Claims, 10 Drawing Sheets

U.S. PATENT DOCUMENTS

| | | |
|---|---|---|
| 6,566,076 B1 | 5/2003 | Dobbs et al. |
| 6,614,946 B1* | 9/2003 | Edgar et al. ............... 382/275 |
| 6,638,770 B1 | 10/2003 | Montagu |
| 6,990,221 B2 | 1/2006 | Shams |
| 7,026,608 B2 | 4/2006 | Hirai |
| 7,076,115 B2 | 7/2006 | Crevier et al. |
| 7,162,101 B2* | 1/2007 | Itokawa et al. ............ 382/282 |
| 7,221,785 B2 | 5/2007 | Curry et al. |
| 7,424,170 B2* | 9/2008 | Steinberg et al. ........... 382/275 |
| 7,504,264 B2* | 3/2009 | Rhode et al. ............... 436/165 |
| 7,522,762 B2* | 4/2009 | Rea et al. .................. 382/141 |
| 7,526,114 B2* | 4/2009 | Xia et al. .................. 382/128 |
| 7,715,596 B2* | 5/2010 | Gehlen et al. .............. 382/118 |
| 2001/0046673 A1 | 11/2001 | French et al. |
| 2002/0085752 A1 | 7/2002 | Ohga |
| 2002/0168665 A1 | 11/2002 | Okawa |
| 2003/0072476 A1 | 4/2003 | Kim et al. |
| 2003/0139886 A1* | 7/2003 | Bodzin et al. ............... 702/28 |
| 2003/0182066 A1 | 9/2003 | Konishi |
| 2004/0032093 A1 | 2/2004 | Razavi |
| 2004/0062773 A1* | 4/2004 | Santiago et al. ........... 424/185.1 |
| 2004/0208350 A1 | 10/2004 | Rea et al. |
| 2004/0229269 A1 | 11/2004 | Hashmi et al. |
| 2004/0241748 A1 | 12/2004 | Ault-Riche et al. |
| 2005/0000811 A1 | 1/2005 | Luka |
| 2005/0038839 A1 | 2/2005 | Ghosh et al. |
| 2005/0090021 A1 | 4/2005 | Walt et al. |
| 2005/0236317 A1 | 10/2005 | Desilets et al. |
| 2005/0244932 A1 | 11/2005 | Harding |
| 2005/0287518 A1 | 12/2005 | Hahn et al. |

OTHER PUBLICATIONS iCycler iQ™ Real-Time PCR Detection System, Instruction Manual, Catalog No. 170-8740, Bio-Rad (Jun. 2003).

Yang, Y.H., et al. "Analysis of cDNA Microarray Images," *Briefings in Bioinformatics*, Henry Stewart Publications, London, GB, vol. 2, No. 4, Dec. 2001, pp. 341-349, XP002335348 ISSN: 1467-5463.

European Patent Office, European Search Report for Application No. 06124151.9-2218 mailed Mar. 9, 2007.

* cited by examiner

|   | 1 | 2 | 3 | 4 | 5 | 6 | 7 | 8 | 9 | 10 | 11 | 12 |
|---|---|---|---|---|---|---|---|---|---|---|---|---|
| A | Pos | Pos | Pos | Pos | Pos | Pos | Pos | Pos | Pos | Pos | Pos | Pos |
| B | Pos | Pos | Pos | Pos | Pos | Pos | Neg | Pos | Neg | Pos | Neg | Pos |
| C | Pos | Pos | Pos | Pos | Pos | Pos | Pos | Pos | Pos | Pos | Pos | Pos |
| D | Pos | Pos | Pos | Pos | Pos | Pos | Neg | Pos | Neg | Pos | Neg | Pos |
| E | Pos | Pos | Pos | Pos | Pos | Pos | Pos | Pos | Pos | Pos | Pos | Pos |
| F | Pos | Pos | Pos | Pos | Pos | Pos | Neg | Pos | Neg | Pos | Neg | Pos |
| G | Pos | Pos | Pos | Pos | Pos | Pos | Pos | Pos | Pos | Pos | Pos | Pos |
| H | Pos | Pos | Pos | Pos | Pos | Pos | Neg | Pos | Neg | Pos | Neg | Pos |

FIG. 4

IMAGE BASED CORRECTION FOR UNWANTED LIGHT SIGNALS IN A SPECIFIC REGION OF INTEREST

BACKGROUND OF THE INVENTION

1. Field of the Invention

This invention relates to a method for correcting signals detected by a detection system in a diagnostic instrument.

2. Discussion of the Art

Raw images generated by a diagnostic instrument having a digital image sensor as a detector, such as, for example, the Applied Biosystems Prism 7000 diagnostic instrument, can exhibit an anomaly known as "cross-talk." Cross-talk refers to the situation where a signal from a given location in the image (for example, a given well in a plate having a plurality of wells, e.g., a 96-well PCR plate), causes a variation in the signal at a different location in the image (for example, a different well in the plate having a plurality of wells). A specific region within an image associated with an independent signal is often referred to as a region of interest (alternatively referred to herein as ROI). Each ROI defines the specific pixels within the image associated with a specific reaction. Variations in signal due to cross-talk, although typically small, can induce variations in reaction quantification of one or more regions of interest within the image. In some cases, sensitivity of the reaction is reduced by requiring an increase in signal threshold in order to avoid false positive results due to cross-talk.

The areas in the image between the regions of interest of the image contain optical information that can be used to compensate for sources of variation in signal. These sources of signal variation can result from a specific geometric optical reflection, scattered light from optical components, light leakage, changes in intensity of the source of light, and the like. All of these sources of variation can contribute to a dynamically changing error in the optical signal in a given region of interest of the image.

It is desired to monitor a region of interest associated with a reaction and ultimately correct for varying anomalous signals over the course of a testing run in a diagnostic instrument.

SUMMARY OF THE INVENTION

In one aspect, this invention provides a method for correcting the signal in an image having a plurality of regions of interest, the method to comprising the steps of:
(a) providing an image having a plurality of regions of interest, these regions of interest having areas between them;
(b) determining a region of correction between at least two regions of interest;
(c) calculating a correction signal from the region of correction; and
(d) using the correction signal to correct a measured signal from one or more regions of interest.

In another aspect, this invention provides a method for defining a region of correction for use in a method for correcting the signal in an image having a plurality of regions of interest, the defining method comprising the steps of:
(a) providing an image having a plurality of regions of interest;
(b) extracting geometric information for a plurality of regions of interest;
(c) selecting a location between at least two regions of interest;
(d) selecting at least one parameter to describe regions of correction; and
(e) constructing regions of correction between the at least two regions of interest.

The regions of correction defined in the forgoing method can be stored for further use to correct signals measured from one or more regions of interest.

The specified regions of correction can have various shapes, such as, for example, circles, squares, diamonds, rectangles, or other geometric figures. Storing of the regions of correction involves determining the definition of the location and the shape of the geometric areas and specifying the pixels contained within each area.

The method of this invention can be used to measure a dynamically changing signal and the effect of the dynamically changing signal on a region of interest of a specific reaction. Correcting for the cross-talk inherent in a dynamically changing signal will greatly increase the sensitivity of the method of detection used in an assay employing such signals. The method of this invention does not affect the optical path of the light collected by a detector. The method can be applied directly to an image that is collected for all the regions of interest.

By measuring the signals in the regions of correction, the signal anomaly due to cross-talk can be significantly reduced.

The sizes and shapes of the regions of correction can vary and depend primarily on the orientation of the existing regions of interest and any image distortions that may be present.

BRIEF DESCRIPTION OF THE DRAWINGS

FIG. 4 is a map of a 96-well plate illustrating the location of each positive response and each negative response.

DETAILED DESCRIPTION

As used herein, the expression "region of interest" means the collection of pixels within an image that define the location of a specific optical signal. The expression "reaction region of interest" means the region of interest associated with a specific reaction in an assay. The expressions "region of correction" and "correction region of interest" mean the area associated with the background portion of the image adjacent to a reaction region of interest. The expression "reaction pixel sum" means the sum of all the pixel intensity values within a reaction region of interest. The expression "reaction pixel count" means the number of pixels within a reaction region of interest. The expression "reaction region of interest pixel average" means the value obtained by dividing the reaction pixel sum by the reaction pixel count. The expression "correction pixel sum" means the sum of all the pixel intensity values within a region of correction. The expression "correction pixel count" means the number of pixels with a region of correction. The expression "region of correction pixel average" means the value obtained by dividing the correction pixel sum by the correction pixel count. The term "scale" means a multiplicative factor applied to the correction calculation. The term "centroid" means the geometric center of a region of interest. As used herein, the terms "circular", "rectangular", "annular", and other terms relating to shape referred to herein are intended to include shapes that are substantially circular, substantially rectangular, substantially annular, and shapes that are substantially similar to the other shapes referred to herein, respectively.

In one aspect, this invention provides a method for correcting an image having a plurality of reaction regions of interest and a plurality of regions of correction, the method involving the steps of:

(a) providing an image having a plurality of regions of interest, these regions of interest having areas between them;
(b) determining a region of correction between at least two regions of interest;
(c) calculating a correction signal from the region of correction; and
(d) using the correction signal to correct a signal measurement from one or more regions of interest.

Figure 3:
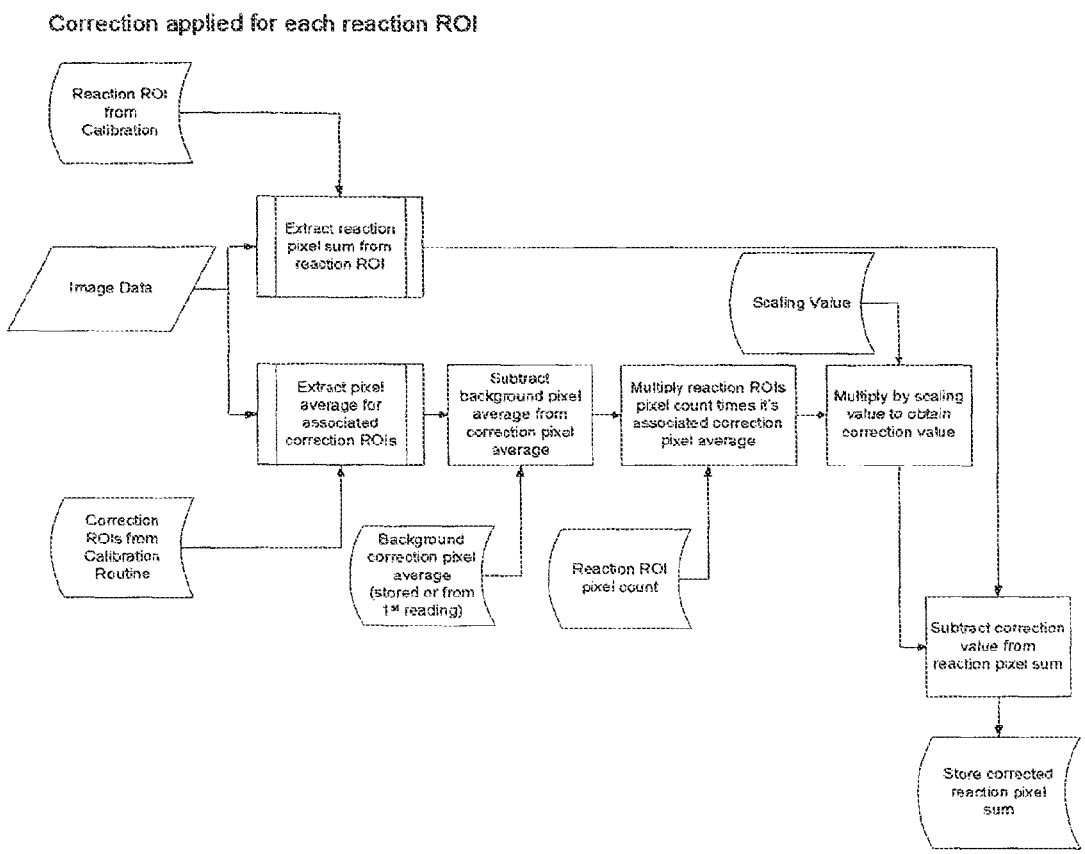
FIG. 3 is a flow chart illustrating the application of the image-based correction algorithm of this invention.

Prior to carrying out the method of this invention, certain steps must be taken to calibrate the imaging system, which is typically a digital imaging system. FIG. 3 shows a flow chart that illustrates steps for defining regions of correction between adjacent reaction regions of interest for the calibration step of the method of this invention. In this flow chart, generic regions of correction are described.

Figure 2A:
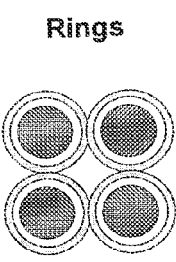
FIG. 2A illustrates one embodiment of reaction regions of interest and regions of correction. The reaction regions of interest are circular and the regions of correction are circular.
Figure 2B:
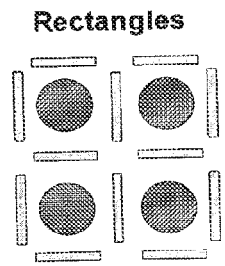
FIG. 2B illustrates another embodiment of reaction regions of interest and regions of correction. The reaction regions of interest are circular and the correction regions of interest are rectangular.
Figure 2C:
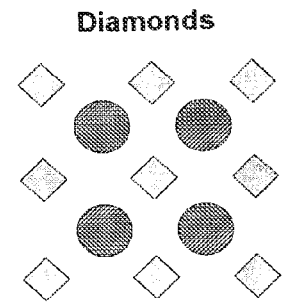
FIG. 2C illustrates still another embodiment of reaction regions of interest and regions of correction. The reaction regions of interest are circular and the regions of correction are shaped like diamonds.

According to the calibration method of this invention, the centroid of each reaction region of interest is determined. The reaction regions of interest are typically determined by using a calibration where signals in a device having a plurality of reaction sites are measured. A signal is measured at each reaction site. In the case of 96-well reaction plates, the signals in a calibration plate containing fluorescent dye at each reaction site can be measured by an imaging sensor. A calibration plate is a 96-well reaction plate used for calibrating the instrument used. The reaction regions of interest can be determined by locating the contiguous pixels at each reaction site within the image. The geometric centroid of each set of centroids from four adjacent reaction regions of interest can be used to determine a center point for a region of correction. A region of correction using that center point and a specific geometric shape can be defined. As shown in FIGS. 2A, 2B, and 2C, the reaction regions of interest are circular in shape. A region of correction can be circular-shaped, as shown in FIG. 2A, rectangular-shaped, as shown in FIG. 2B, or diamond-shaped, as shown in FIG. 2C. Other shapes, such as, for example, closed polygons, are suitable for both the reaction regions of interest and the regions of correction. The parameters of the regions of correction are typically radii of rings for circular-shaped regions of correction, length and width for rectangular-shaped regions of correction, and length of sides for diamond-shaped regions of correction. Dimensions for the particular geometric shape selected are specified. An alternative to defining regions of correction by means of geometric shapes involves the use of an arbitrary bitmap. Such a bitmap could, for example, be a 9 by 9 array of values specifying which pixels would be included in the region of correction and which pixels would be excluded from the region of correction. The center points of the regions of correction can be mirrored to create regions of correction on the periphery of the plate for the outer rows and columns of the reaction regions of interest in the image. Thus, in the case of diamond-shaped regions of correction in an image having 96 reaction regions of interest, there are 117 diamond-shaped regions of correction of interest in total, i.e., four (4) diamond-shaped regions of correction per reaction region of interest. The use of diamond-shaped regions of correction is shown in FIG. 2C. The regions of interest associated with specific wells can be determined and stored, such as, for example, by means of a computer. In this embodiment, each reaction region of interest has the four adjacent regions of correction associated with it.

Similarly, in the case of rectangular-shaped regions of correction in an image having a plurality of reaction regions of interest (e.g., 96 wells in a plate), the rectangles can be oriented with the length parallel to the x-axis or to the y-axis, as shown in FIG. 2B. For the x-direction (horizontal), the center point between two adjacent regions of interest is located. A rectangle is constructed by using the center point between two adjacent regions of interest as the center of the region of correction between the regions of interest. For the y-direction (vertical), the center point between two adjacent regions of interest is located. The rectangle is constructed by using the center point between two adjacent regions of interest as the center of the region of correction between the regions of interest. Rectangles are also created on the periphery of the image for the outer rows of regions of interest and outer columns of regions of interest. The mirror of the center between adjacent regions of interest is used to set the center of the region of correction rectangle. The regions of interest associated with specific wells can be determined and stored. In this embodiment, each reaction region of interest has the four adjacent regions of correction associated with it. Measures other than the centroid of the regions of correction can also be used to define the location of regions of correction. For example, the region of correction can be placed equidistant from boundaries of adjacent regions of interest.

After the region of correction calibration is performed, the correction based upon from the region of correction can be applied by using the following method. Once the region of correction calibration is performed, a background offset value needs to be generated. This value can be generated in at least two ways. According to a first alternative, a background calibration can be performed. In this method, an image is taken of a plate without any fluorescent dye. During the background calibration, the average pixel value for each region of correction is calculated by dividing the pixel sum by the pixel count in that region of correction to obtain an average pixel value. This average pixel value is indicative of the background light level and is referred to as the background offset value. The background offset values are stored for use in future runs, e.g., PCR runs. Alternatively, the background offset value can be determined on a run-by-run basis by calculating the average pixel value for each region of correction for the first reading of a run, e.g., a PCR run. Because the first (or first few) readings of a PCR run occur before a significant reaction signal is produced, this alternative method provides a good representation of the background.

Figure 1:
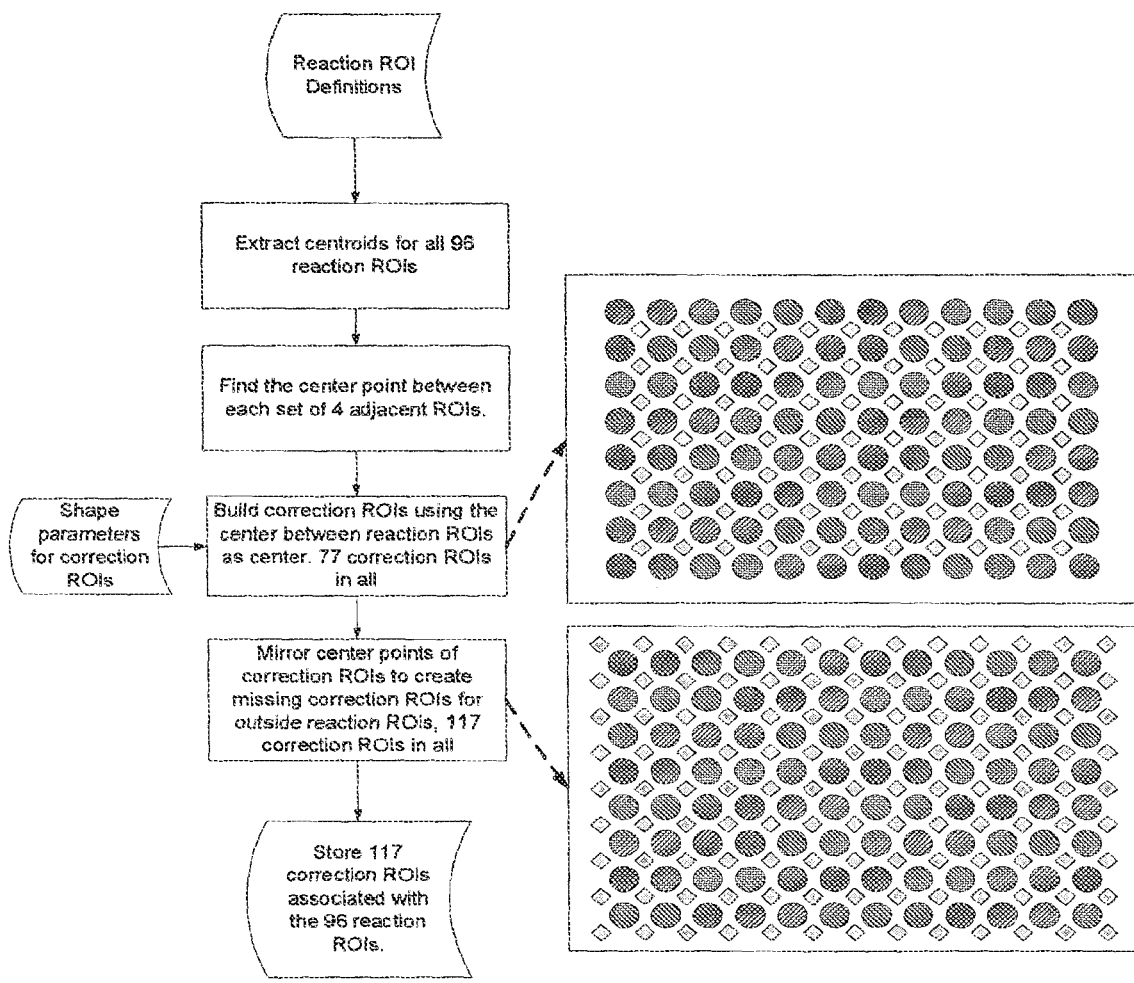
FIG. 1 is a flow chart that defines the placement of diamond-shaped regions of correction about circular reaction regions of interest.

The signal correction is performed in the following manner. Performance of signal correction is depicted in FIGS. 1 and 3. For each reaction, the reaction pixel sum and the reaction pixel count are calculated by using the reaction region of interest. The average pixel value for the four regions of correction associated with a given reaction region of interest is calculated. Although four regions of correction are shown in FIG. 1 and diamond-shaped regions of correction are shown in FIG. 1, the method is not limited to four regions of correction nor is the invention limited to diamond-shaped regions of correction. The background offset value is subtracted from the region of correction pixel average. Then, this difference is multiplied by the reaction region of interest pixel count and, if necessary, by a scale factor, to generate a correction value. The correction value is then subtracted from the reaction region of interest pixel sum to generate a corrected reaction region of interest pixel sum. The scale factor is typically dependent upon the detection system. An example of a scale factor is 1.15. In some instrument systems, multiple exposures are made at each reading to increase the dynamic range of measurement. In this case, a corresponding background offset and region of correction pixel average needs to be generated for each exposure. The correction to the reaction pixel sum is then made for the exposure of longest duration that does not exhibit significant saturation of the image sensor.

This invention can also be applied to an assay system based on array or a microarray, such as, for example, the Vysis GenoSensor genomic DNA microarray system (Abbott Laboratories, Abbott Park, Ill.). Such systems can measure a plurality of genomic targets through hybridization to an array of capture targets placed on a surface, such as, for example, a glass "chip" or a microscope slide. The product of the hybridization is typically measured by means of fluorescent dyes and an electronic imaging system.

The following non-limiting example further explains the method of this invention.

EXAMPLE

A real time PCR run for HIV was performed on an ABI Prism 7500 instrument (Applied Biosystems, Foster City, Calif.). This instrument utilizes a 96-well plate format with wells arranged in a 12×8 array. The run was configured so that there were 84 wells containing positive samples with a concentration of $1 \times 10^6$ copies/mL and 12 wells not containing positive samples, i.e., negative wells. The negative wells were distributed on the plate to maximize the potential cross-talk from the wells containing positive samples. FIG. 4 illustrates the layout of the plate.

Figure 5:
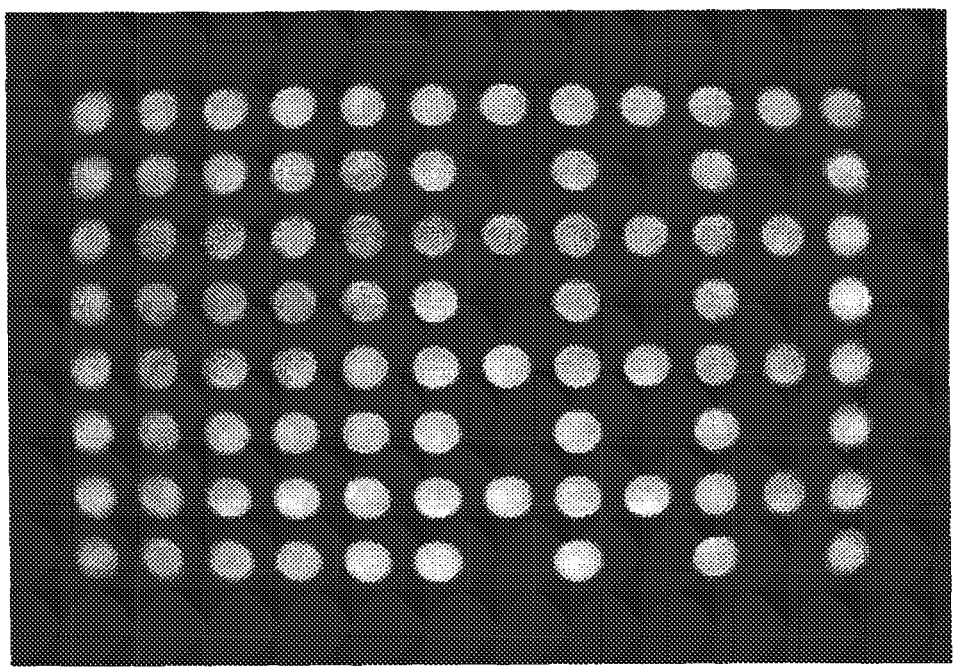
FIG. 5 is a sample of an image at the end of a run.
Figure 6:
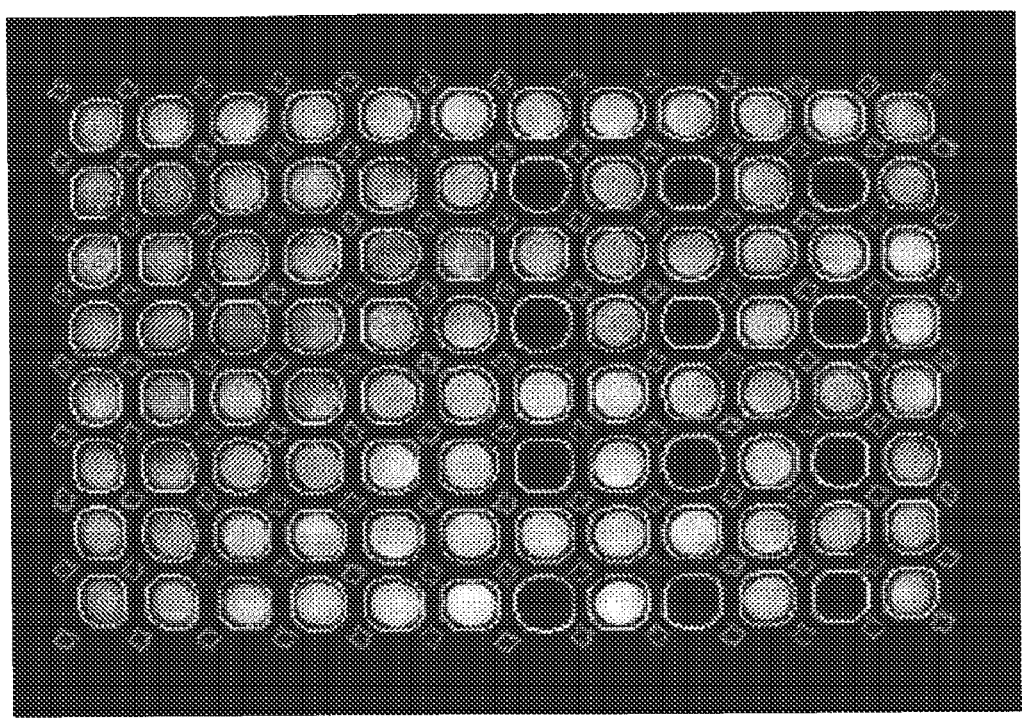
FIG. 6 is a sample of an image showing reaction regions of interest and regions of correction.

The ABI Prism 7500 instrument uses a CCD camera and measures fluorescence in five wavelength bands. FIG. 5 shows one image from the end of the PCR run. FIG. 6 shows the same image with the reaction regions of interest and the regions of correction superimposed. In this example, a diagonal array of diamond-shaped regions of correction, each of which contained of 25 pixels, were used. The first reading in the PCR run was used to establish the background offset values for each subsequent reading. The scaling factor used was 1.15.

Figure 7:
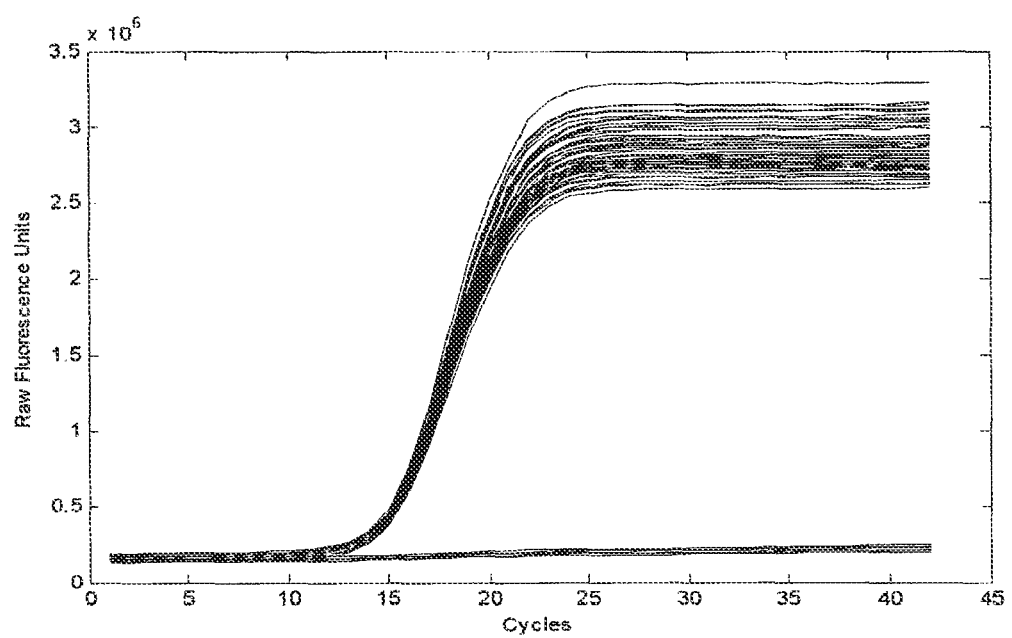
FIG. 7 shows fluorescence responses in a PCR assay without image-based correction applied.
Figure 8:
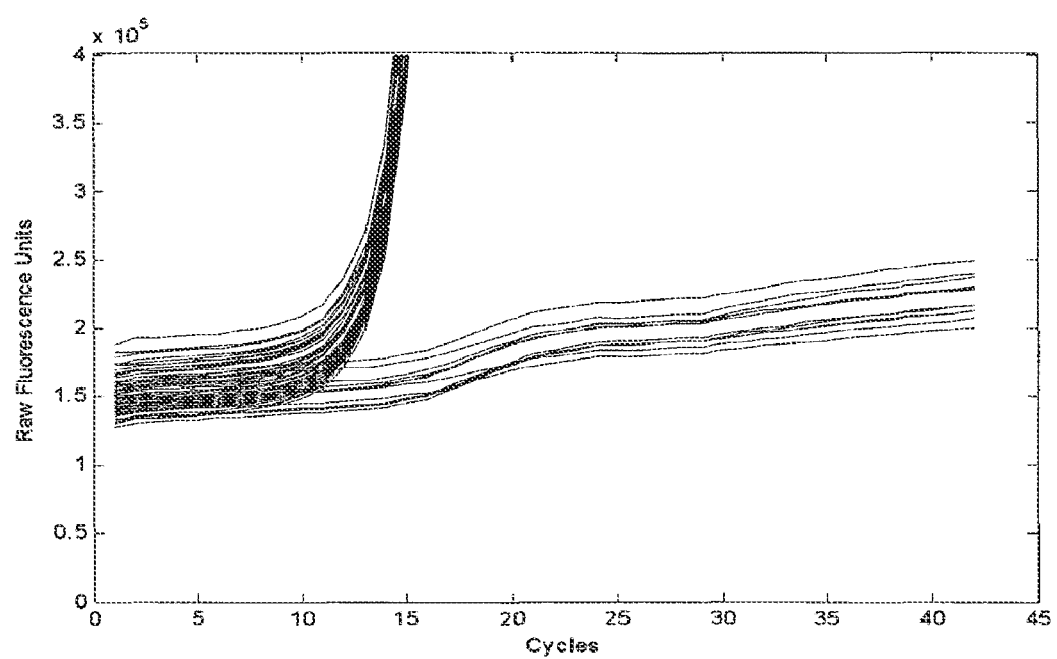
FIG. 8 shows fluorescence responses in a PCR assay without image-based correction applied. In this figure, the Y scale is expanded.
Figure 9:
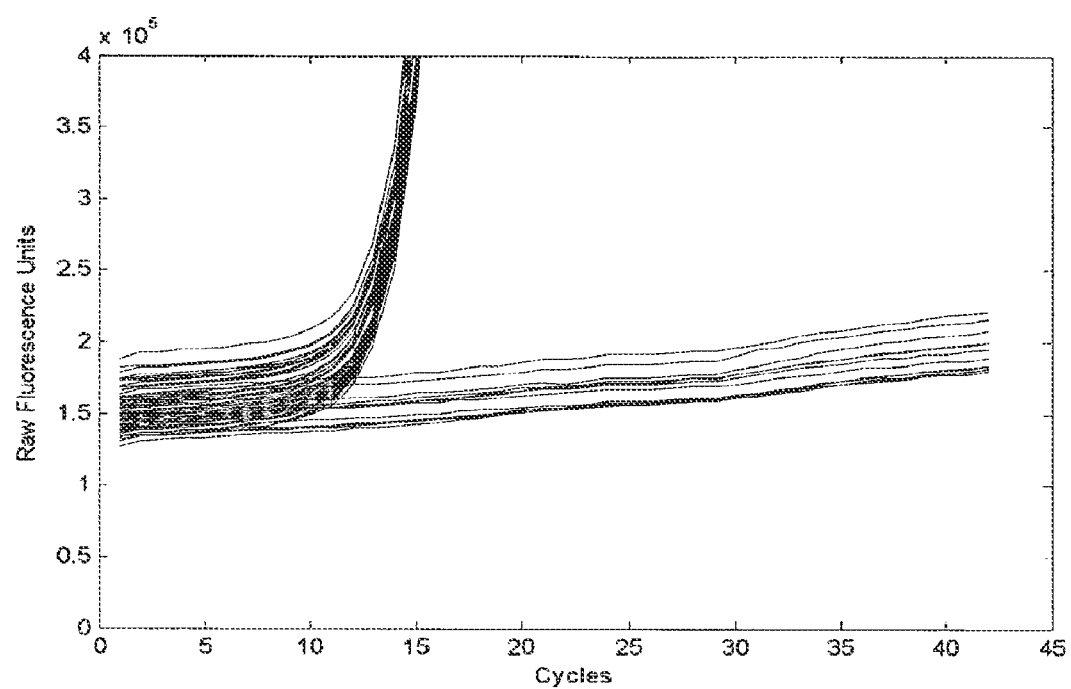
FIG. 9 shows fluorescence responses in a PCR assay with image-based correction. In this figure, the Y scale is expanded.
Figure 10:
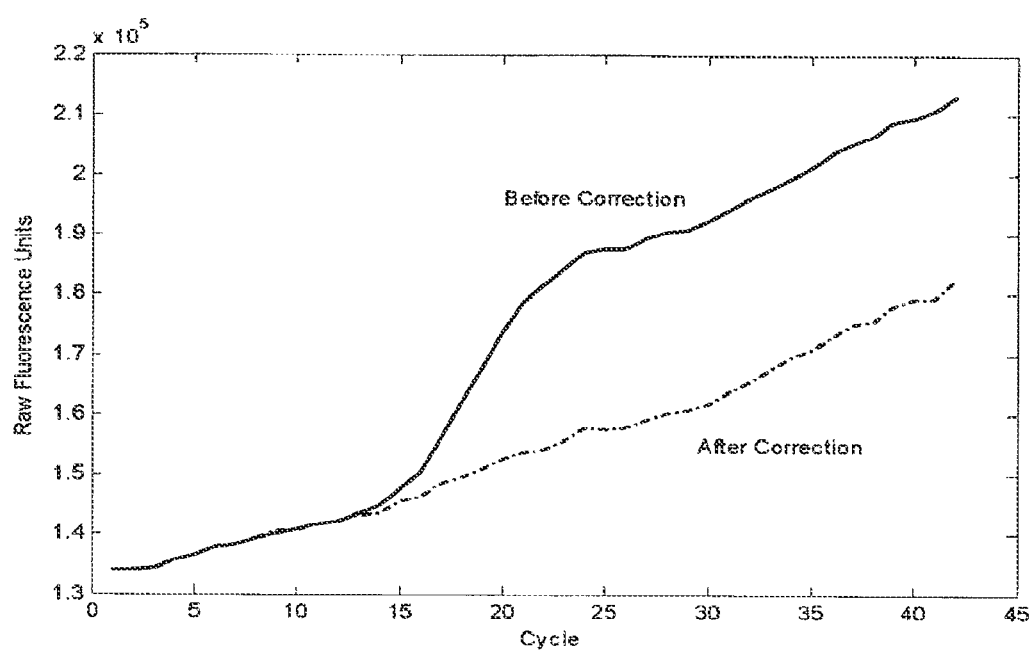
FIG. 10 shows the fluorescence response in a PCR assay for well F-11 from FIG. 4 with and without assay-based correction.

FIG. 7 shows the raw fluorescence signals for all 96 samples without any image-based correction applied. As can be seen, the 84 positive samples generated signals significantly above the background fluorescence by cycle 15 and approached their maximum fluorescence by cycle 25. FIG. 8 shows the same responses with the Y-axis scaled to focus on the responses in wells not containing positive samples. All of the negative responses showed a small but significant rise from cycles 15 through 25, which is caused by cross-talk from the responses of the positive samples. FIG. 9 shows the effect of the image-based correction on the negative responses. As can be seen, the cross-talk signal has been effectively eliminated. FIG. 10 shows the response for well F-11 with and without the image-based correction applied.

The method is also applicable to images that contain a fewer or a greater number of regions of interest.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for correcting the signal in an image having a plurality of regions of interest, the method comprising the steps of:
    (a) providing an image having a plurality of regions of interest, these regions of interest having areas between them;
    (b) extracting geometric information for the plurality of regions of interest;
    (c) selecting at least one parameter to describe a region of correction the at least one parameter defining a shape of the region of correction;
    (d) determining the region of correction between at least two regions of interest based on the extracted geometric information for the plurality of regions of interest and the at least one parameter selected to describe the region of correction;
    (e) calculating a correction signal from the region of correction; and
    (f) using the correction signal to correct a signal measurement from the at least two regions of interest and reduce cross-talk between the at least two regions of interest.

2. The method of claim 1, further including the step of determining a background signal and adjusting the correction signal of a run by subtracting the background signal from the correction signal.

3. The method of claim 2, wherein the background signal is a background signal stored prior to commencing the run.

4. The method of claim 2, wherein the background signal is a background signal determined during the run.

5. The method of claim 1, wherein the correction signal is scaled.

6. The method of claim 1, wherein the region of correction has a plurality of sides.

7. The method of claim 1, wherein the region of correction has four sides.

8. The method of claim 1, wherein the region of correction is a closed polygon.

9. The method of claim 1, wherein the region of correction is circular.

10. The method of claim 1, wherein the region of correction is annular.

11. The method of claim 1, wherein the region of correction is defined by a bitmap.

12. The method of claim 1, wherein said plurality of regions of interest are from a multi-well plate.

13. The method of claim 1, wherein a thermocycler reader is employed.

14. The method of claim 1, further including the step of storing the region of correction defined in step (d).

15. A method for defining a region of correction for use in a method for correcting the signal in an image having a plurality of regions of interest, the defining method comprising the steps of:
   (a) providing an image having a plurality of regions of interest;
   (b) extracting geometric information for the plurality of regions of interest;
   (c) selecting a location between at least two regions of interest based on the extracted geometric information for the plurality of regions of interest;
   (d) selecting at least one parameter to describe the region of correction, the at least one parameter defining a shape of the region of correction; and
   (e) constructing the region of correction between the at least two regions of interest based on the at least one parameter selected to describe the region of correction and the location selected between the at least two regions of interest, wherein the region of correction reduces cross-talk between the plurality of regions of interest.

16. The method of claim 15, further including the step of constructing additional regions of correction that are not between the at least two regions of interest.

17. The method of claim 16, wherein a sufficient number of additional regions of correction are constructed so that each region of interest has the same number of regions of correction as does any other region of interest.

18. The method of claim 15, wherein the geometric information for the region of interest is a centroid.

19. The method of claim 18, wherein the location between at least two regions of interest is the center point between the centroids of at least two regions of interest.

20. The method of claim 15, wherein the region of correction is selected from the group consisting of polygons, circles, annuli, and bitmaps.

21. The method of claim 15, further including the step of storing the region of correction associated with the at least two regions of interest.

22. A method for correcting the signal in an image having a plurality of regions of interest, the method comprising the steps of:
   (a) providing an image having a plurality of regions of interest, these regions of interest having areas between them;
   (b) extracting geometric information for the plurality of regions of interest;
   (c) determining a region of correction between at least two regions of interest based on the extracted geometric information for the plurality of regions of interest;
   (d) calculating a correction signal from the region of correction;
   (e) determining a background signal and adjusting the correction signal of a run by subtracting the background signal from the correction signal; and
   (f) using the adjusted correction signal to correct a signal measurement from the at least two regions of interest and reduce cross-talk between the at least two regions of interest.

23. The method of claim 22, wherein the background signal is a background signal stored prior to commencing the run.

24. The method of claim 22, wherein the background signal is a background signal determined during the run.

* * * * *